(12) United States Patent
Lin et al.

(10) Patent No.: US 7,122,688 B2
(45) Date of Patent: Oct. 17, 2006

(54) USE OF FUNCTIONALIZED MESOPOROUS SILICATES TO ESTERIFY FATTY ACIDS AND TRANSESTERIFY OILS

(75) Inventors: Victor Shang-Yi Lin, Ames, IA (US); Daniela Rodica Radu, Ames, IA (US)

(73) Assignee: Iowa State University Research Foundation, Ames, IA (US)

( * ) Notice: Subject to any disclaimer, the term of this patent is extended or adjusted under 35 U.S.C. 154(b) by 0 days.

(21) Appl. No.: 10/945,559

(22) Filed: Sep. 20, 2004

(65) Prior Publication Data
US 2005/0107624 A1 May 19, 2005

Related U.S. Application Data

(60) Provisional application No. 60/511,863, filed on Oct. 16, 2003.

(51) Int. Cl.
*C11C 3/00* (2006.01)
(52) U.S. Cl. .................................... 554/169; 585/502
(58) Field of Classification Search ................ 554/169; 585/502
See application file for complete search history.

(56) References Cited

U.S. PATENT DOCUMENTS

| 5,051,533 A | 9/1991 | Verkade |
| 5,525,126 A | 6/1996 | Basu et al. |
| 6,204,424 B1 * | 3/2001 | Yadav et al. ................ 585/502 |

FOREIGN PATENT DOCUMENTS

EP 0566047 A2 10/1993

OTHER PUBLICATIONS

"Methyl Soyate Shows Promise as Natural Solvent", *Feedstocks*, 3(2), (1998), 4 pgs.
"Physical and Cleaning Performance Properties of Methyl Soyate", *Report, USB Project No. 7429*, Omnitech International, Ltd. (1997), 1 pg.
"Process Pumps Up Biodiesel's Potential", *2003 Annual Report, Plant Sciences Institute*, (2003), 1 pg.
"Soy Methyl Ester Solvents—Technical Background", *United Soybean Board (USB) Newsletter*, (2002), 2 pgs.
Beck, J. S., et al., "A New Family of Mesoporous Molecular Sieves Prepared With Liquid Crystal Templates", *Journal of the American Chemical Society*, 114(27), (1992), 10834-10843.
Beck, J. S., et al., "Molecular or Supramolecular Templating: Defining the Role of Surfactant Chemistry in the Formation of Microporous and Mesoporous Molecular Sieves", *Chemistry of Materials*, 6(10), (1994),1816-1821.
Bender, M., "Economic Feasibility Review for Community-Scale Farmer Cooperatives for Biodiesel", *Bioresource Technology*, 70, (1999),81-87.

(Continued)

*Primary Examiner*—Deborah D. Carr
(74) *Attorney, Agent, or Firm*—Schwegman, Lundberg, Woessner & Kluth (57) ABSTRACT

The present invention provides a method to prepare a fatty acid lower alkyl esters from a feedstock, such as a vegetable or an animal oil, comprising one or more fatty acid glycerol esters such as mono-, di- or tri-glycerides, and free fatty acids, comprising combining the feedstock, a lower alcohol and an acidic mesoporous silicate under conditions wherein the mesoporous silicate catalyzes the formation of the corresponding fatty acid lower alkyl ester of the free fatty acids an optionally glycerol.

19 Claims, 8 Drawing Sheets

OTHER PUBLICATIONS

Boocock, D. G., et al., "Fast Formation of High-Purity Methyl Esters from Vegetable Oils", *JAOCS*, 75(9), (1998),1167-1172.

Bossaert, W. D., et al. "Mesoporous Sulfonic Acids as Selective Heterogeneous Catalysts for the Synthesis of Monoglycerides", *Journal of Catalysis*, 182(1), (1999),156-164.

Diasakou, M., et al., "Kinetics of the Non-Catalytic Transesterification of Soybean Oil", *Fuel*, 77(12), (1998),1297-1302.

Diaz, I., et al., "A Direct Synthesis Route to the Mesoporous Silicate SBA-2 Bearing Thiol Groups", *Studies in Surface Science and Catalysis*, 135, (2001),1248-1253.

Diaz, I., et al., "Combined Alkyl and Sulfonic Acid Functionalization of MCM-41-Type Silica", *Journal of Catalysis*, 193, (2000),295-302.

Diaz, I., et al., "Synthesis of MCM-41 Materials Functionalised With Dialkylsilane Groups and Their Catalytic Activity in the Esterification of Glycerol With Fatty Acids", *Applied Catalysis A: General*, 242, (2003),161-169.

Encinar, J. M., et al., "Preparation and Properties of Biodiesel from *Cynara cardunculus* L. Oil", *Industrial & Engineering Chemistry Research*, 38(8), (1999),2927-2931.

Freedman, B., et al., "Transesterification Kinetics of Soybean Oil", *JAOCS*, 63(10), (1986),1375-1380.

Huh, S., et al., "Organic Functionalization and Morphology Control of Mesoporous Silicas via a Co-Condensation Synthesis Method", *Chemistry of Materials*, 15(22), (2003),4247-4256.

Kildiran, G., et al., "*In-situ* Alcoholysis of Soybean Oil", *JAOCS*, 73(2), (1996),225-228.

Kruk, M., "Characterization of the Porous Structure of SBA-15", *Chemistry of Materials*, 12(7), (2000),1961-1968.

Lim, M. H., et al., "Synthesis of Ordered Microporous Silicates with Organosulfur Surface Groups and Their Applications as Solid Acid Catalysts", *Chemistry of Materials*, 10(2), (1998),467-470.

Lin, V. S.-Y., "Molecular Recognition Inside of Multifunctionalized Mesoporous Silicas: Toward Selective Fluorescene Detection of Dopamine and Glucosamine", *Journal of the American Chemical Society*, 123(46), (2001), 11510-11511.

Ma, F., et al., "Biodiesel Fuel From Animal Fat. Ancillary Studies on Transesterification of Beef Tallow", *Industrial & Engineering Chemistry Research*, 37, (1998),3768-3771.

Margolese, D., et al., "Direct Syntheses of Ordered SBA-15 Mesoporous Silica Containing Sulfonic Acid Groups", *Chemistry of Materials*, 12(8), (2000),2448-2459.

Mbaraka, I. K., "Organosulfonic Acid-Functionalized Mesoporous Silicas for the Esterification of Fatty Acid", *Journal of Catalysis*, 219, (2003), 329-336.

Melero, J. A., et al., "Direct Synthesis of Ordered SBA-15 Mesoporous Materials Containing Arenesulfonic Acid Groups", *Journal of Materials Chemistry*, 12, (2002),1664-1670.

Ogoshi, T., et al., "Soap and Related Products: Palm and Lauric Oil", *JAOCS*, 62(2), (1985),331-335.

Stein, A., et al., "Hybrid Inorganic-Organic Mesoporous Silicates-Nanoscopic Reactors Coming of Age", *Advanced Materials*, 12(19), (2000),1403-1419.

Suppes, G. J., et al., "Calcium Carbonate Catalyzed Alcoholysis of Fats and Oils", *JAOCS*, 78(2), (2001),139-145.

Tanev, P. T., "A Neutral Templating Route to Mesoporous Molecular Sieves", *Science*, 267(5199), (1995),865-867.

Van Rhijn, W. M., et al., "Sulfonic Acid Functionalised Ordered Mesoporous Materials as Catalysts for Condensation and Esterification Reactions", *Chemical Communications*, (3), (1998),317-318.

Wildes, S. G., "TA 91-1997—Market Opportunity Summary—Soy-Based Solvents", *United Soybean Board (USB)*), (1997), 2 pgs.

Ying, J. Y., et al., "Synthesis and Applications of Supramolecular-Templated Mesoporous Materials", *Angewandte Chemie International Editions*, 38, (1999),56-77.

Zhao, D., et al., "Triblock Copolymer Syntheses of Mesoporous Silica With Periodic 50 to 300 Angstrom Pores", *Science*, 279, (1998),548-552.

\* cited by examiner

USE OF FUNCTIONALIZED MESOPOROUS SILICATES TO ESTERIFY FATTY ACIDS AND TRANSESTERIFY OILS

CROSS-REFERENCE TO RELATED APPLICATION

This application claims priority under 35 U.S.C. 119(e) to U.S. Provisional Application No. 60/511,863, filed Oct. 16, 2003, which application is incorporated herein by reference.

GOVERNMENT FUNDING

This invention was made with Government support of the United States Department of Agriculture, Natural Resources Conservation Service: NRCS 68-3A75-3-146. The United States Government has certain rights in this invention.

BACKGROUND OF THE INVENTION

Recently, advances have been made which strike a more desirable balance between maintaining fuel efficiency and reducing the percentage of particulate emissions in fuels through the use of blends of petroleum based fuel with alkyl esters of the fatty acids contained in vegetable oils or animal fats. These alkyl esters are commonly referenced to as "biodiesel". Substantially pure alkyl esters, such as methyl or ethyl esters of fatty acids, are generally preferred in biodiesel over the use of the vegetable oils and animal fats themselves because the alkyl esters have a viscosity that is more appropriate to diesel fuel. Through the use of these fuel blends, researchers have attained reductions in particulate emissions from diesel engines. See, e.g., M. Bender, *Bioresource Technol.*, 70, 81 (1999); M. Diasakou et al., *Fuel*, 77, 1297 (1998); T. Ogoshi et al., *J. Am. Oil Chem. Soc.*, 62, 331 (1985).

The production of biodiesel has received also extensive interest as a result of this fuel's desirable renewable, biodegradable, and nontoxic properties. See, e.g., G. J. Suppes et al., *J. Am. Oil Chem. Soc.*, 78, 839 (2001); G. Kildrian et al., *op. cit.*, 73, 225 (1996); J. Encinar et al., *Ind. Eng. Chem. Res.*, 38, 2927 (1999). These fatty acid alkyl esters can be prepared by the transesterification of triglycerides in vegetable oils with short-chain alcohols (e.g., methanol and ethanol) using homogeneous alkali catalysts such as alkoxides. For example, soy diesel (methyl soyate) is made commercially by an energy and labor-intensive process wherein soybean oil is reacted with methanol at 140–150° F. (sometimes under pressure) in the presence of sodium methoxide. Isolation of the desired methyl soyate from the highly caustic (toxic) catalyst and other products such as glycerol, involves a precise neutralization process with strong acids, such as hydrochloric acid (HCl), and extensive washes with water to remove the resulting sodium chloride (NaCl) salt. Also, because of glycerol's high boiling point, it must be separated from the sodium chloride salt by vacuum distillation in an energy intensive operation. As more alkyl soyates with different alkyl functional groups, such as ethyl and isopropyl soyates, are being rapidly developed to meet the growing needs of various applications, the level of difficulty in separating the corresponding catalysts, e.g., sodium ethoxide and sodium isoproxide catalysts, respectively, will unavoidably escalate due to the increasing solubility of these basic catalysts in the reaction mixture. Therefore, biodiesel is currently not cost competitive with conventional diesel fuel.

To improve the economic outlook of biodiesel and alkyl esters in general, the feedstock selection becomes critical. In particular, oil feeds containing high free fatty acid content, such as found in beef tallow or yellow grease, are significantly less expensive than vegetable oils, such as soybean or rapeseed oil (F. Ma et al., *op. cit.*, 37, 3768 (1998). These high free fatty acid feedstocks present significant processing problems in standard biodiesel manufacture since the free fatty acid is saponified by the homogeneous alkali catalyst that is used to transesterify triglycerides leading to a loss of catalyst as well as increased purification costs (D. G. B. Boocock et al., *J. Am. Oil Chem. Soc.*, 75, 1167 (1998).

One approach for improving the processing of high free fatty acid oils is to first esterify the free fatty acids to alkyl esters in the presence of an acidic catalyst such as a mineral acid. The pretreated oils in which the free fatty acid content is lowered to no more than 0.5 wt % can then be processed under standard transesterification reaction conditions (H. N. Basu et al. (U.S. Pat. No. 5,525,126)). This pretreatment step has been successfully demonstrated using sulfuric acid (S. Koona et al., European Pat. No. 566047 (1993)). Unfortunately, use of the homogeneous sulfuric acid catalyst adds neutralization and separation steps as well as the esterification reaction to the overall process.

Surfactant-templated mesostructured materials have received a great deal of attention as potential catalysts, sensors and adsorption agents owing to their combination of extremely high surface areas and ordered, flexible pore sizes. For example, mesoporous sieves of the type MCM-41 are prepared by thermal treatment of silaceous gels formed by the polymerization of alkoxysilanes around surfactant micelle templates in aqueous base, followed by removal of the surfactant to yield a matrix comprising fine pores in a cylindrical array. The physical and chemical properties of these mesoporous materials can be modified by incorporating functionalized organic groups, either by grafting on the preformed mesopore surface or by co-condensation using functionalized substituted trialkoxy silanes during synthesis. See, e.g., D. Zhao et al., *Science*, 279, 548 (1998); A. Stein et al., *Adv. Materials*, 12, 1403 (2000); and W. M. Van Rhijn et al., *Chem. Commun.*, 317 (1995). Organic-inorganic hybrid mesoporous silicas formed by co-condensation with thio-containing silanes, followed by oxidation of the SH groups yield pores functionalized with sulfonic acid groups. The direct co-condensation synthesis technique in which the mesostructure and functional group are simultaneously introduced, appears to be a desirable route for incorporating functional groups because it has been shown that it increases the concentration of the sulfonic groups in the mesoporous silica relative to post-formation grafting (I. Diaz et al., *Stud. Surf. Sci. Catal.*, 135, 1248 (2001). One approach demonstrated previously involves one-step synthesis based on the simultaneous hydrolysis and condensation of tetraethoxysilane (TEOS) with 3-(mercaptopropyl)trimethoxysilane (MPTMS) in the presence of template surfactant using in situ oxidation of the thiol groups with $H_2O_2$. Melero et al. has shown that the acid strength of the sulfonic groups in the mesoporous materials can be adjusted by choice of the organosulfonic precursor (J. A. Melero et al., *J. Mater. Chem.*, 12, 1664 (2002).

For example, mesoporous catalysts containing sulfonic acid groups and, optionally internal methyl groups have been reported to be efficient catalysts in the esterification of glycerol with fatty acids, where high yields of mono-esters are obtained. See, e.g., W. D. Bossaert et al., *J. Catal.*, 182, 156 (1999); I. Diaz et al., *Appl. Catal. A.*, 242, 161 (2003); I. Diaz et al., *J. Catal.*, 193, 295 (2000); D. Magolese et al.,

*Chem. Mater.*, 12, 2448 (2000). Similar SO$_3$H silicates have been used to tetrahydropyranylate ethanol. M. H. Lin et al., *Chem. Mater.*, 10, 467 (1998). Mesoporous silica functionalized with arenesulfonic acid groups has been used to catalyze the Fries rearrangement of phenyl acetate to 2- and 4-hydroxyacetophenones. J. A. Melero et al., *J. Mater. Chem.*, 12, 1664 (2002).

However, a continuing need exists for a simple method to form (lower)alkyl esters of fatty acids in the environment of triglyceride-containing feedstocks.

SUMMARY OF THE INVENTION

The present invention provides a method to prepare a fatty acid ($C_1$–$C_3$) alkyl esters from a feedstock, such as a vegetable or an animal oil, comprising one or more fatty acid glycerol esters such as mono-, di- or tri-glycerides, and free fatty acids, comprising combining the feedstock, a ($C_1$–$C_3$) alcohol and an acidic mesoporous silicate under conditions wherein the mesoporous silicate catalyzes the formation of the corresponding fatty acid ($C_1$–$C_3$) alkyl ester of the free fatty acids and optionally glycerol. Thus, in one embodiment, the present invention provides a method to transesterify an ester comprising combining the ester, a ($C_1$–$C_3$) alcohol and an acidic mesoporous silicate under conditions wherein the mesoporous silicate catalyzes the formation of the ($C_1$–$C_3$) alkyl ester of the acid portion of the ester and the corresponding free alcohol of the ester. In another embodiment, the present invention provides a method to prepare a lower alkyl ester of a fatty acid comprising combining the fatty acid, a lower alkanol and an acidic mesoporous silicate under conditions wherein the silicate catalyzes the formation of the corresponding lower (alkyl) ester. In a preferred embodiment, the fatty acid is present in an organic or synthetic feedstock such as an animal or vegetable oil that comprises a major portion of glycerol fatty acid esters.

Preferably the fatty acid portion of the ester or glyceride is derived from a ($C_8$–$C_{22}$) fatty acid, preferably a ($C_{10}$–$C_{18}$) fatty acid, which is a saturated alkyl ester that optionally comprises 1–3 CH=CH moieties in the alkyl chain. The ($C_1$–$C_3$) alcohols are preferably methanol, ethanol, propanol or i-propyl alcohol, although higher alkanols such as ($C_4$–$C_6$) alkanols may be useful in some applications. The alcohol is preferably used in a molar excess over the starting material acid and/or ester component of the feedstock, since such esterification/transesterification reactions are highly reversible.

The acidic mesoporous silicate is preferable particulate or granular, and can have a preselected shape such as spherules or rods. The pore size must be sufficient to admit triglycerides and/or fatty acids, and to permit the release of fatty acid esters and/or glycerol. Pore sizes preferably can range from about 1.0–50 nm, preferably about 2–10 nm in diameter. Larger diameters may be useful to process certain oils. The silicate comprises acidic groups immobilized by linkage to the interior pores and optionally to the exterior surface of the silicate matrix. Useful acidic groups comprise sulfonic acids, sulfinic acids, phosphoric acids, phosphinic acids, boronic acids, selenic acids and mixtures thereof, preferably linked to the silicate matrix via inert organic groups, such as alkyl, fluoroalkyl, alkenyl, arakyl, alkaryl, aryl, fluoroaryl, and the like. Thus, the functionalized mesoporous silicate functions as a bioinert, heterogenous catalyst that can be readily separated from the reaction products.

Preferably, the esterification/transesterification reaction is carried out at a relatively low temperature, e.g., of about 20–150° C. Although solvent may not be necessary for liquid feedstocks, the reaction can be carried out in the presence of a polar aprotic solvent such as an ether, e.g., THF, dialkylethers, alkoxypolyols, and the like.

As used herein, the term animal oil or vegetable oil includes triglyceride-containing materials from plants (seeds and vegetables), mammals, birds and fish and includes those materials that are solid at room temperature (fats such as lard, tallow, hydrogenated vegetable oils, grease, etc.) as well as materials recognized as oils, such as soybean oil, olive oil, safflower oil, sunflower seed oil, linseed oil, cottonseed oil and the like.

As used herein, the term "alkyl" includes ($C_1$–$C_{12}$) alkyl; "lower(alkyl)" includes ($C_1$–$C_3$) alkyl.

Soybean oil typically contains triglycerides of oleic acid 26%, of linoleic acid 49%, of linolenic acid 11%, of saturated [alkyl] acids 14%. Free fatty acids are usually less than 1%. Phospholipids (lecithin) 1.5–4%. Another 0.8% consists of stigmasterol, sitoserols, and tocopherols. The phospholipids can be removed by refining with alkali.

Thus, in preferred embodiments, the invention provides a method to use sulfonic acid-functionalized mesoporous solid silicate catalysts to effectively convert fatty acid-containing oil feedstocks to the corresponding fatty acid esters (biodiesel) and triglycerides that can be further processed to yield fatty acid esters and glycerol. The use of such catalysis provides several advantages over conventional transesterification/esterification: 1. The ability to convert fatty acids into esters in alcohol containing solutions, so that the free fatty acid-containing oils, animal fats, and restaurant deep-fry oils can be used as feedstocks for biodiesel production. 2. The catalysts are solids that function as heterogeneous catalysts that can be separated from the reaction mixture and recycled. 3. The catalysts have high surface areas because of their porosity. 4. The pores are sufficiently large to allow passage of the soybean oil and alcohols used in the transesterification process through them. 5. The pores can be chemically modified to allow more rapid passage of large molecules such as vegetable oil molecules through them. 6. The catalyst rapidly and under mild conditions converts soybean oil to soybean oil methyl ester plus glycerol (which are easily mechanically separated). The methyl ester (biodiesel) is a viable biodegradable alternative to petroleum-based fuels. Glycerol has a variety of cosmetic and food uses, but it is also under investigation as a biodegradable alternative to petroleum-based ethylene glycol and propylene glycol in aviation de-icing formulations.

BRIEF DESCRIPTION OF THE FIGURES

FIG. 2 depicts scanning electromicrographs 2(*a*) and 2(*b*) of the mesoporous materials functionalized as shown in FIGS. 1(*a*) and 1(*b*), respectively.

DETAILED DESCRIPTION OF THE INVENTION

Hereinbelow is described the synthesis and utilization of silica mesoporous materials modified with sulfonic groups for the pretreatment esterification of high free fatty acid oils. The results for the catalytic performance of the mesoporous materials are also compared to commercial acid catalysts.

Mesoporous Silicates

Particulate mesoporous silicates typically have a particle size of about 50 nm to about 1 μm. In one embodiment, the mesoporous silicates have a particle size of at least about 100 nm, or preferably at least about 200 nm. In another embodiment, the mesoporous silicates have a particle size of less than about 750 nm. As conventionally prepared, they are spherical, but they have also been prepared under conditions that yield other shapes such as rods. The catalysts of the invention can include mesoporous silicates of any shape, provided the pore structure is suitable for admitting the feedstock acids and/or esters.

The mesoporous silicate pores typically have a diameter of from about 1–100 nm. In one embodiment of the invention, the pores have a diameter of at least about 2 nm. In other embodiments, the pores have diameters of greater than about 5 nm, or greater than about 10 nm. Typically, the pores have a diameter of less than about 75 nm or less than about 50 nm.

The acidic mesoporous silicates can be prepared from aqueous dispersions of surfactant micelles of surfactants such as ($C_{10}$–$C_{20}$)alkylamines, $C_{10}$–$C_{16}$ alkyl(tri(lower) alkyl)ammonium salts or Pluronic® surfactants in water, followed by introduction of an alkyl orthosilicate, such as tetraethylorthosilicate (TEOS), and one or more functionalized silanes, comprising one or more functional groups that is sufficiently acidic or that can be converted into an acid, such as sulfonic acid, such as one more ($C_2$–$C_{20}$)alkyl, aryl, fluoroalkyl, fluoroaryl, alkaryl, arakyl, alkaralkyl, arylakenyl, alkenyl, alkenylaryl, or aralkenyl groups substituted with mercapto, chloro, bromo, amino, carboxy, alkoxycarbonyl, sulfonyl or alkynyl-, wherein aryl is preferably $C_8$–$C_{10}$ aryl and the ($C_2$–$C_{10}$)alkyl chain(s) are optionally interrupted by —S—S—, amido (—C(=O)NR—), —O—, ester (—C(=O)O—), and the like. Optionally, silanes functionalized with groups such as ($C_1$–$C_3$)alkyl, aryl, aralkyl, alkaryl, $CF_3$ and the like can be co-condensed with the "acidic silanes" to further modify the properties of the surface and of the pores of the silicates. The aqueous mixture is stirred at moderate temperatures until the silicate precipitates, and it is collected and dried. The surfactant "template" is then removed from the pores of the ordered silicate matrix, for example, by refluxing the silicate in aqueous-alcoholic HCl. The remaining solvent can be removed from the pores of the silicate by placing it under high vacuum and/or by heating. The functional groups incorporated on the surface of the pores can be quantified and optionally, can be further modified as by oxidation, reaction with a protected acid equivalent followed by deprotection to yield the acidic silicate, and the like.

For example, starting components to prepare a representative neutral mesoporous silicate, MCR-4, include one or more quaternary alkyl ammonium surfactants which are added in water to tetraethoxysilane or tetramethoxysilane, optionally followed by additional surfactant. The resulting gel is agitated for another 0.25–60 min. and is divided over two autoclaves. The hydrothermal step is carried out dynamically at about 350–400 K. The resulting white product is filtered, washed extensively with hot $H_2O$ and EtOH, dried at elevated temperatures in air, and finally calcined for 5–15 h. See, J. S. Beck, *J. Amer. Chem. Soc.,* 114, 10834 (1992).

Propylsulfonic acid mesoporous silicas. Mesoporous silicas can be modified with a 3-mercapto lower($C_1$–$C_4$)alkyl group using (3-mercapto($C_1$–$C_3$)alkyl)trimethoxy(or triethoxy)silane as the organosulfonic acid precursor. Deposition of the mercaptoalkyl silane in inert solvent onto a silicate support with controlled water content results in a "coated" material with a monolayer of mercaptoalkyl moieties, while less-covered "silylated" materials are obtained under dry conditions. Alternatively, in the synthesis of a hexagonal mesoporous silica, organofunctional groups are directly incorporated by "co-condensation" of mercaptoalkylsilance and the main Si source (the tetralkoxysilane) in the presence of a neutral surfactant such as a Pluronic®. Representative recipes for the different synthesis procedures are based on literature examples in W. D. Bossaert et al., *J. Catal.,* 182, 156 (1999) and are given below.

Coated MCM-41-SH. Calcined MCM-41 is hydrated by refluxing for 106 h in water and removed from the suspension by filtration. The wet filter cake is suspended in toluene in a Dean Stark apparatus, and $H_2O$/toluene is removed until a translucent suspension is obtained. An excess of mercaptoalkyl silane is added and after stirring overnight without heating, the suspension is refluxed for 1–5 h. The coated material is then washed in a Soxhlet extractor with $CH_2Cl_2$/$Et_2O$ (50/50) and dried.

Silylated MCM-41-SH. Calcined MCM-41 is evacuated (overnight, 375–400 K, <10 Pa) and added to a solution of mercaptoalkyl silane in toluene. Toluene was dried over zeolite 4A before use. After 4 h refluxing, the powder is collected and subjected to the same Soxhlet purification as the previous material.

Coated silica gel-SH. This was prepared by modifying a chromatographic silica gel 60 (70–230 mesh, Fluka) with mercaptoalkyl silane following the same method as used to coat MCM-41.

CDAB-SH prepared by co-condensation. CDAB-SH was synthesized at room temperature from a gel containing 0.8 parts tetraalkoxysilane, 0.2 parts mercaptopropyl tri(alkoxy) silane, 0.275 parts surfactant, in 100 parts lower(alkanol) and water. The surfactant was first dissolved in the alcohol-water mixture. Then the silane mixture was added and the mixture was stirred for 24 h. The amine template was extracted from the as-synthesized CDAB—SH with boiling EtOH.

Oxidation procedure and acidification. Materials with immobilized mercaptoalkyl groups were oxidized with $H_2O_2$ or nitric acid in a alkanol water mixture. Typically, aqueous 35% $H_2O_2$ dissolved in three parts of methanol is used per g of material. After a suitable time, the suspension is filtered, and washed with $H_2O$ and lower(alkanol). The wet material was resuspended (1 wt %) in acidified H$_2$O for another 2–7 h. Finally, the materials are extensively rinsed with H$_2$O, dried at an elevated temperature and stored in a desiccator. These acid-activated materials are denoted with the suffix —SO$_3$H.

The mesoporous materials in the examples below were synthesized following the co-condensation procedures of Boessaert et al., *J. Catalysis,* 182, 56 (1999) and Melero et al., *J. Mater. Chem.,* 12 1664 (2002) with only slight modifications. Tetraethoxysilane (TEOS, 98%, Aldrich) was used as the silica source. The mesoporous silicas were modified using 3-(mercaptopropyl)-trimethoxysilane (MPTMS, 85%, Fluka) without further treatment. The surfactants, CDAB (cetyldimethyl(ethyl)ammonium bromide) (Aldrich), Pluronic® L64 and Pluronic® P123 (BASF Co., USA), were used as purchased. Mesoporous silica synthesized using the CDAB is denoted as CDAB, while those synthesized with the tri-block Pluronic® copolymers were abbreviated SBA-15. See, A. Stein, *Adv. Mater.,* 12, 1403 (2000).

EXAMPLE 1

CDAB-SO$_3$H

A molar composition of 0.08 TEOS, 0.02 MPTMS, 0.0275 CDAB, 0.89 EtOH and 2.94 H$_2$O was used to synthesize CDAB-SH. The amino surfactant was dissolved in an alcohol-water mixture prior to addition of the TEOS-MPTMS mixture. The mixture was aged for 24 hrs at room temperature under continuous stirring. The resulting solid product was filtered and air-dried. The amine template was extracted by refluxing in boiling EtOH for 24 hrs. The thiol groups were oxidized with H$_2$O$_2$ (2.04 g/g solid) in a methanol-water mixture. The suspension was stirred at room temperature for 24 hrs followed by washing with EtOH and H$_2$O. The wet cake was acidified in 0.1 M H$_2$SO$_4$ for an additional 4 hrs before being washed thoroughly with H$_2$O. The product was then dried at 393 K.

EXAMPLE 2

SBA-15-SO$_3$H

SBA-15-SO$_3$H was prepared by dissolving 4 g of Pluronic® surfactant (P123 or L64) in 125 g of 1.9 M HCl at room temperature under stirring with subsequent heating to 40° C. before adding TEOS. Approximately 45 min. was allowed for prehydrolysis of TEOS prior to addition of the MPTMS-H$_2$O$_2$ solution. The resulting mixture with a molar composition of 0.0369 TEOS, 0.0041 MPTMS, and 0.0369 H$_2$O$_2$ was stirred for 24 hrs at 40° C. and thereafter aged for 24 hrs at 100° C. under static conditions. The product was collected and subjected to the same extraction method as previously described.

EXAMPLE 3

SBA-15-ph-SO$_3$H

Figure 1:
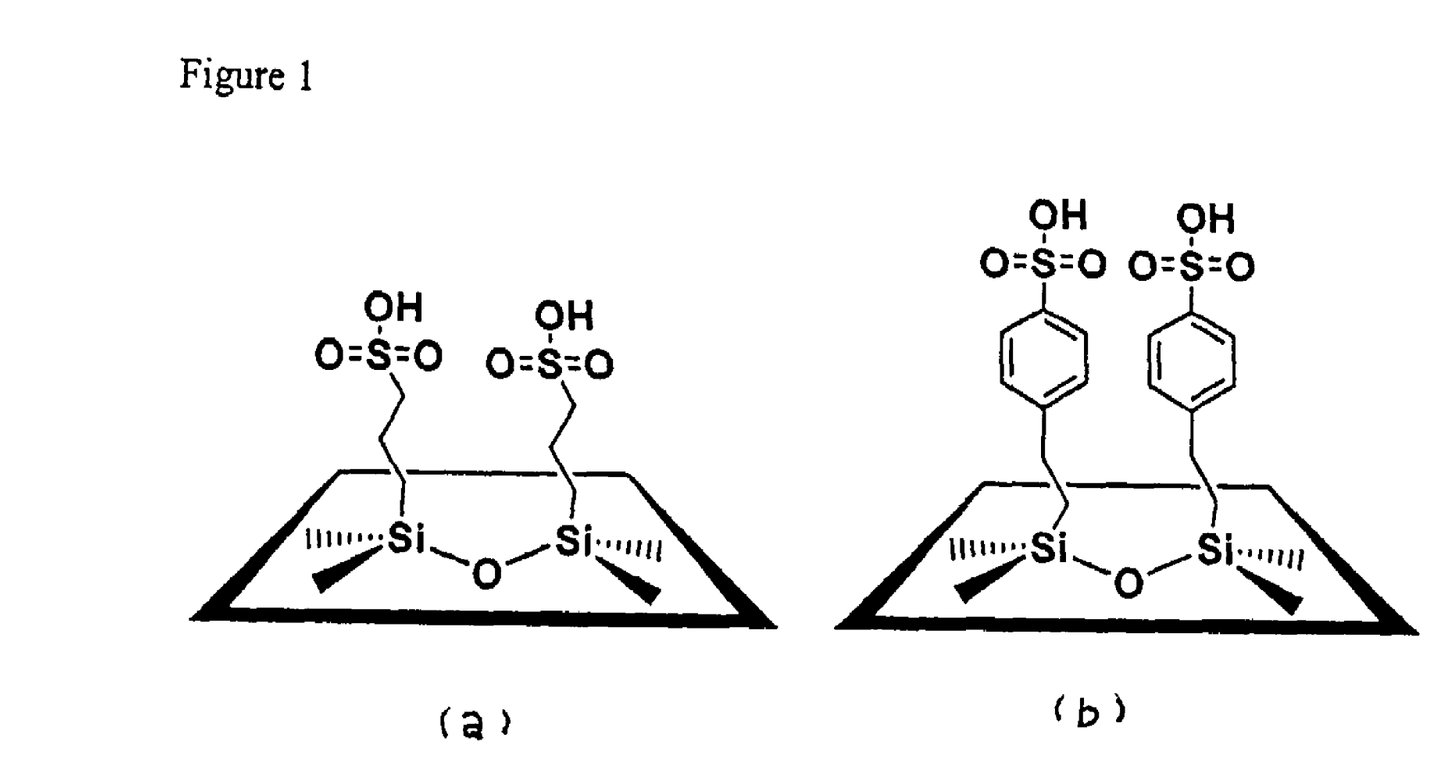
FIG. 1 depicts mesoporous materials with two organosulfonic acid functional groups; a) propylsulfonic groups, b) arenesulfonic groups.

SBA-15-ph-SO$_3$H mesoporous silica functionalized with benzenesulfonic acid groups was synthesized as follows. Pluronic® P123 surfactant (4 g) was dissolved with stirring in 125 ml of 1.9 M HCl at room temperature. After complete dissolution, the solution was heated to 35° C. TEOS (8.76 g) was added dropwise to the solution at a constant temperature of 35° C. After a TEOS prehydrolysis of 45 min, 2.66 mL of 2-(4-chlorosulfonylphenyl)ethyltrimethoxysilane (CSPTMS) solution in methylene chloride (50%, Gelest) was added dropwise (to prevent phase separation). The resulting mixture was stirred for 20 hrs at 35° C. following by aging at 95° C. for another 24 hrs. The molar composition of the mixture for 4 g of copolymer was: 7.4 TEOS:1 CSPTMS:48 HCl:1466 H$_2$O. The solid was isolated via filtration, washed extensively with methanol and dried in the air. The surfactant template was removed by suspending the solid material in ethanol and refluxing for 48 hours. The sulfonyl chloride groups underwent hydrolysis in the acidic media of the reaction. Shown in FIG. 1 are the respective oragnosulfonic acid functional groups introduced into the silicate lattice.

EXAMPLE 4

Synthesis of TPES-MCM Material

To synthesize the TPES-functionalized mesoporous silica (TPES-MCM), the well-developed cetyltrimethylammonium bromide (CTAB) surfactant-templated co-condensation method of tetraethoxysilane (TEOS) and organosiloxane precursors was modified by using compound 1 as the organosiloxane precursor, as shown in Scheme A.

Synthesis of Compound 1:

2,2'-Dipyridyl disulfide (8.82 g, 40.0 mmol) was dissolved in 50.0 mL of methanol; 1.6 mL of glacial acetic acid was added as catalyst. To this mixture, 2-mercaptoethanesulfonic acid sodium salt (3.82 g, 20.0 mmol) in 30.0 mL of methanol was added dropwise in 30 min with stirring. The reaction mixture was protected from light and stirred at ambient temperature overnight, followed by solvent evaporation under vacuum. The crude product was repurified by dissolving in a small amount of methanol, followed by ethyl ether precipitation and dried under vacuum to yield compound 1a. 5.14 g, yield=94.0%. $^1$H-NMR (300 MHz; DMSO-d$_6$), δ 2.73 (m, 2H, CH$_2$), 3.02 (m, 2H, CH$_2$), 7.24 (d, 1H, ArH), 7.81 (m, 2H, ArH) 8.45 (d, 1H, ArH).

To synthesize 2-[3-(trimethoxysilyl)-propyldisulfanyl]-ethanesulfonic acid sodium salt (1), compound 1a (1.36 g, 5.0 mmol) was dissolved in 20.0 mL of methanol with 1.0 mL of glacial acetic acid. To this mixture, (3-mercaptopropyl)trimethoxysilane (0.95 mL, 5.0 mmol) in 10.0 mL of methanol was added dropwise. The mixture was protected from light and stirred under nitrogen at room temperature overnight. The reaction mixture was quenched and solvent was evaporated under vacuum. The solid obtained was dissolved in a small amount of methanol, followed by ethyl ether precipitation. The purified product was collected by filtration and dried under vacuum. 5.14 g, yield=74.7%. $^1$H-NMR (300 MHz; $D_2O$) δ 0.79 (t, 2H, $CH_2(1)$), 1.83 (q, 2H, $CH_2(2)$), 2.81 (t, 2H, $CH_2(3)$, 3.03 (t, 2H, $CH_2(5)$), 3.27 (t, 2H, $CH_2(4)$), 3.60 (s, 7H, $OCH_3$).

Sodium hydroxide (0.83 g, 20.84 mmol) was dissolved in 80.0 mL (5.0×10$^3$ mmol) of deionized water, and 1.53 g (4.17 mmol) CTAB was added while stirring continuously to get a clear solution, and then compound 1 (1.24 g, 3.46 mmol) was added. The reaction mixture was stirred at ambient temperature for two hours, followed by dropwise addition of TEOS (6.97 mL, 31.27 mmol). The mixture was stirred vigorously at room temperature for two days followed by heating at 90° C. for one day to improve the structural order. The as-synthesized TPES-MCM was filtered off, and then dried at 90° C. under vacuum for 10 h. To remove the surfactant template, 3.0 g of as-synthesized TPES-MCM was refluxed for 24 hours in 9.0 mL 37.4% HCl/324.0 mL MeOH.

EXAMPLE 5

Characterization and Testing of Acidic Mesoporous Silicates

A. Characterization.

The textural properties of the mesoporous materials were measured using the BET procedure. Nitrogen adsorption-desorption isotherms were taken at 77 K using a Micromeritics ASAP 2000 system. The ion capacities of the sulfonic acid groups in the functionalized mesoporous silica were quantified using 2 M NaCl as the ion-exchange agent. Approximately 0.05 g of the sample was added to 15 ml of the salt solution and allowed to equilibrate. Thereafter, it was titrated by dropwise addition of 0.01 M NaOH (O. Margolese et al., *Chem. Mater.*, 12, 2448 (2000).

B. Catalytic Tests

The reagents used for the catalytic test included palmitic acid (PA, ≧95%, Sigmna), refined soybean oil (SBO, Wesson) and methanol (MeOH, ≧99.9%, Fisher Scientific). A model high free fatty acid oil feed was simulated using 15% wt PA in SBO. The oil mixture was charged into the 100 ml reaction vessel with MeOH at a ratio of 1:20 w/w (PA:MeOH). The esterification reactions were performed in a stainless steel high-pressure batch reactor, Series 4565 Bench Top Mini Reactor (Parr Instrument Co., USA) fitted with mechanical stirrer and sample outlet. The reaction vessel was held at constant temperature with the aid of the heating mantle and integrated water cooling system. Catalysts were screened using different loadings (5–20% w/w of the PA). The range of reaction temperature studied was 65 to 120° C. Samples were drawn at hour intervals and their acid values were determined using the AOCS method Cd 3a-63.

Shown in FIG. 1 are the respective organosulfonic acid functional groups used in the study. The catalytic activities of the functionalized mesoporous silicas were compared with several commercial catalysts, including homogeneous catalysts (sulfuric acid and p-toluenesulfonic acid, pTSA) from Fisher Scientific and heterogeneous catalysts, Nafion NR50 (SA=0.02 m$^2$/g, H$^+$ capacity=0.8 meq/g, Alfa Aesar Co. USA) and Amberlyst-15wet (SA=45 m$^2$/g, Dp=250 Å, H$^+$ capacity=4.7 meq/g, Rohm and Haas Co. USA). All experiments were performed at least twice to evaluate reproducibility.

C. Results and Discussion

The textural properties of the funtionalized mesoporous silicas synthesized for the current work are summarized in Table 1, where the suffix designates the surfactant used.

TABLE 1

| | | Textural properties | | | |
|---|---|---|---|---|---|
| Catalyst | Surfactant | $S_{BET}$ ($m^2g^{-1}$) | $V_P$ ($cm^3g^{-1}$) | $D_P$ (Å) (MPD) | H$^+$ meq/g Sample |
| CDAB-SO$_3$H—C12 | CDAB | 778 | 0.39 | 28 | 0.60 |
| SBA-15-SO$_3$H-L64 | Pluronic L64 | 820 | 0.58 | 27 | 0.84 |
| SBA-15-SO$_3$H-P123 | Pluronic P123 | 735 | 0.67 | 35 | 1.44 |
| SBA-15-ph-SO$_3$H-P123 | Pluronic P123 | 540 | 0.71 | 50 | 0.92 |

The N$_2$ adsorption-description isotherms of the synthesized samples had the hysteresis behavior associated with mesoporous materials (see, e.g., P. T. Tanev et al., *Science*, 267, 865 (1995) and M. Kruk et al., *Chem. Mater.*, 12, 1961 (2000). The shape of the hysteresis loop indicated that the mesopores were disordered, which is a characteristic of mesoporous silica synthesized using either neutral or nonionic surfactants as templates.

As seen in Table 1, the median pore diameter (MPD) of the mesoporous materials as determined by the BJH method was dependent on the surfactant template used, which is consistent with previous reports, and can be attributed to the size of the micelle structure formed during synthesis. See, e.g., J. S. Beck et al., *J. Amer. Chem. Soc.*, 114, 10834 (1992), J. S. Beck et al., *Chem. Mater.*, 6, 1816 (1994). For the propylsulfonic acid functionalized samples, CDAB—SO$_3$H—C16 had the smallest MPD of 21 Å (2.1 nm). The CDAB material is formed from the cooperative self-assembly of the cetyldimethy(ethyl)ammonium bromide (C$_{16}$), with a neutral silica precursor. This procedure yields mesoporous materials with worm-like pore structure and large wall thickness (See, H. Seong et al., *Chem. Mater. ASAP*, web release Oct. 3, 2003). The pore diameter of the CDAB material strongly depends on the length of the aliphatic carbon chain of the surfactant. The SBA materials were synthesized using Pluronic® L64 and P123 surfactants, which are tri-block copolymers of poly(ethylene oxide)-block-poly(propylene oxide)-block-poly(ethylene oxide), with molecular structure of EO$_{13}$—PO$_{30}$-EO$_{13}$ and EO$_{20}$-PO$_{70}$-EO$_{20}$, respectively (J. Y. Ying et al., *J. Angew. Chem. Int. Ed. Eng.*, 38, 56 (1999)). The SBA-15-SO$_3$H—P123 sample gave the largest MPD among the propylsulfonic acid functionalized silicas. The larger MPD from use of Pluronic® P123 can be attributed to the lower EO:PO ratio of Pluronic® P123 relative to Pluronic® L64, 0.29 and 0.43, respectively. The decreased EO:PO ratio, which is a result of an increase in the molecular weight of the propylene oxide in the copolymer, increases the hydrophobicity of the resulting micelles. The increase in hydrophobicity of the micelles will increase their size leading to an enlarged MPD in the resulting mesoporous material.

The BET surface area of the samples was in the range reported in the literature for the mesoporous materials, which validates that the solvent extraction of the surfactant was successful. No clear relation between the surface areas of the functionalized mesoporous silica and the surfactant template was observed.

The pore size distributions for the propylsulfonic acid functionalized silicas are calculated from the BJH method. The unimodal pore diameter distribution is consistent with that reported for organo-modified mesoporous silicas synthesized with either neutral or nonionic surfactants. The pore volume followed the same trend with surfactant as was observed for the MPD. There was no apparent correlation between the pore volume and the BET surface area.

The number of sulfonic acid groups in the mesoporous silica, which were determined quantitatively using acid-base titration, are given in Table 1. It is noteworthy that the acid capacity of the materials was found to increase with increasing MPD. This result was unexpected given that equal concentrations of the MPTMS and the oxidation reagent were used in the synthesis of all the samples. This difference indicates that all the sulfur must not reside in the sulfonic acid groups. It is possible the oxidation process that converts the thiol in the MPTMS precursor to the sulfonic acid group may also be oxidizing some of the adjacent thiol groups to disulfides, which would not be reactive.

The reaction performance of the functionalized mesoporous silicas was evaluated for the esterification of free fatty acids in a fatty acid/triglyceride mixture. A mixture of 15 wt % palmitic acid in soybean oil was used as the model high free fatty acid feed. This free fatty acid content is consistent with the value expected for a typical yellow grease. The transesterification of vegetable oil, which is performed with a homogeneous alkali catalyst such as sodium hydroxide or sodium methoxide, runs best using a feedstock with <0.5 wt % free fatty acid due saponification of the free fatty acid with the alkali catalyst. Transesterification of oil feeds with higher concentrations of free fatty acid leads to low yields and high production costs due to this depletion of the catalyst and subsequent formation of soap, which increases purification costs (see, U.S. Pat. No. 5,525,126). Pretreatment of a high free fatty acid oil via acid catalyzed esterification of the free fatty acid would provide a means for producing a feedstock that could be used in a standard transesterification reaction system. Therefore, the performance objective of the acid catalyst with the model feed is to decrease the palmitic acid content to less than <0.5 wt %. The esterification reaction is performed in excess methanol to favor the forward reaction, since the esterification of fatty acids with alcohol is extremely reversible.

Figure 3:
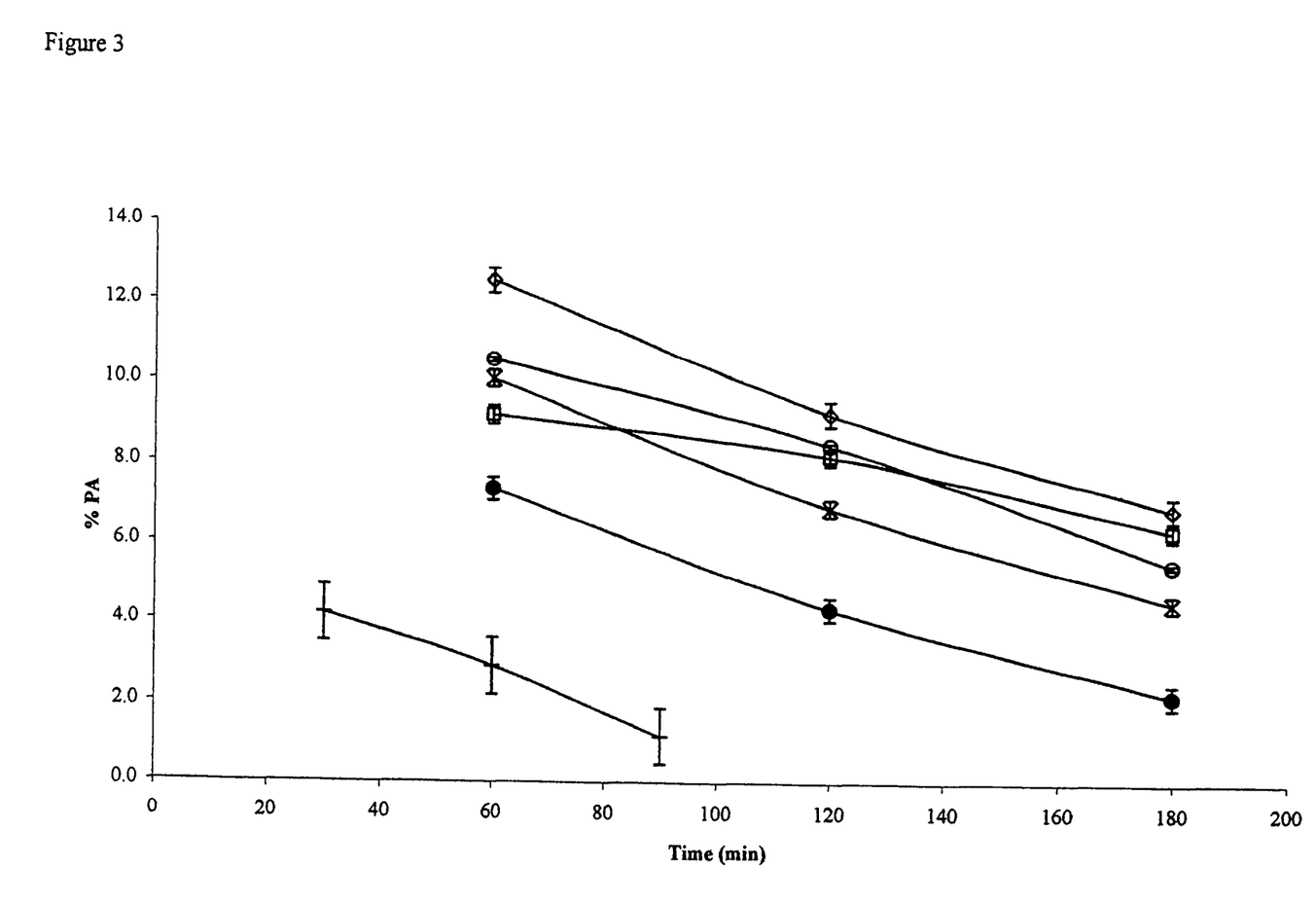
FIG. 3 is a graph depicting the catalytic results of esterification of palmitic acid in soybean oil with methanol over different catalysts (85° C.; PA:MeOH=1:20, catalyst: +=5% H$_2$SO$_4$, •=10% SBA-15-SO$_3$H—P123, ×=10% Nafion, ○=10% SBA-15-SO$_3$H-L64, □=10% CDAB—SO$_3$H—C16, ◇=10% Amberlyst 15wet).

To provide a comparison basis for the functionalized mesoporous silicas, the esterification reaction was also performed with $H_2SO_4$ and two commercial acidic resins, Amberlyst-15 and Nafion. Shown in FIG. 3 are the results for reaction studies performed at 85° C. with a methanol to palmitic acid ratio of 20:1 by weight. The figure gives the palmitic acid concentration by weight as a function of reaction time. A catalyst concentration of 10 wt % was used for all of the catalysts except $H_2SO_4$, which was used at only 5 wt % concentration. As can be seen from the figure, the $H_2SO_4$ homogeneous catalyst is the most active with a conversion of more than 90% in less than 1.5 hr. The high activity of $H_2SO_4$ is consistent with results reported in the literature, where as low as 5 wt % loading of the cid was reported to be sufficient to esterify free fatty acids to levels of less than 0.5 wt % (B. Freedman et al., *J. Amer. Oil Chem. Soc.*, 63, 1375 (1986)).

Among the functionalized mesoporous silicas, SBA-15-$SO_3H$—P123 gave the highest catalytic activity and CDAB—$SO_3H$—C16 gave the least, with palmitic acid conversions of 85% and 55%, respectively, after 3 hr. The higher activity with SBA-15-$SO_3H$—P123 is consistent with the material having the largest number of active sites (1.44 meq/g sample) as well as the largest pore diameter (35 Å). This observation is consistent with that reported by W. D. Bossaert et al., *J. Catal.*, 182 156 (1999) for the esterification of gylcerol with lauric acid (dodecanoic acid) using propylsulfonic acid functionalized mesoporous silica catalysts.

As seen in FIG. 3, Amberlyst-15 despite its high exchange capacity gave the least catalytic activity with a conversion of 40%, while the Nafion was intermediate relative to the mesoporous silica catalysts with a conversion of 70%. Amberlyst-15 is known to be an active catalyst in a number of esterification reactions and Nafion contains highly acidic sites, however, their low activity suggests that either their catalytic sites are not accessible or under the given reaction conditions they are not sufficiently reactive.

Figure 4:
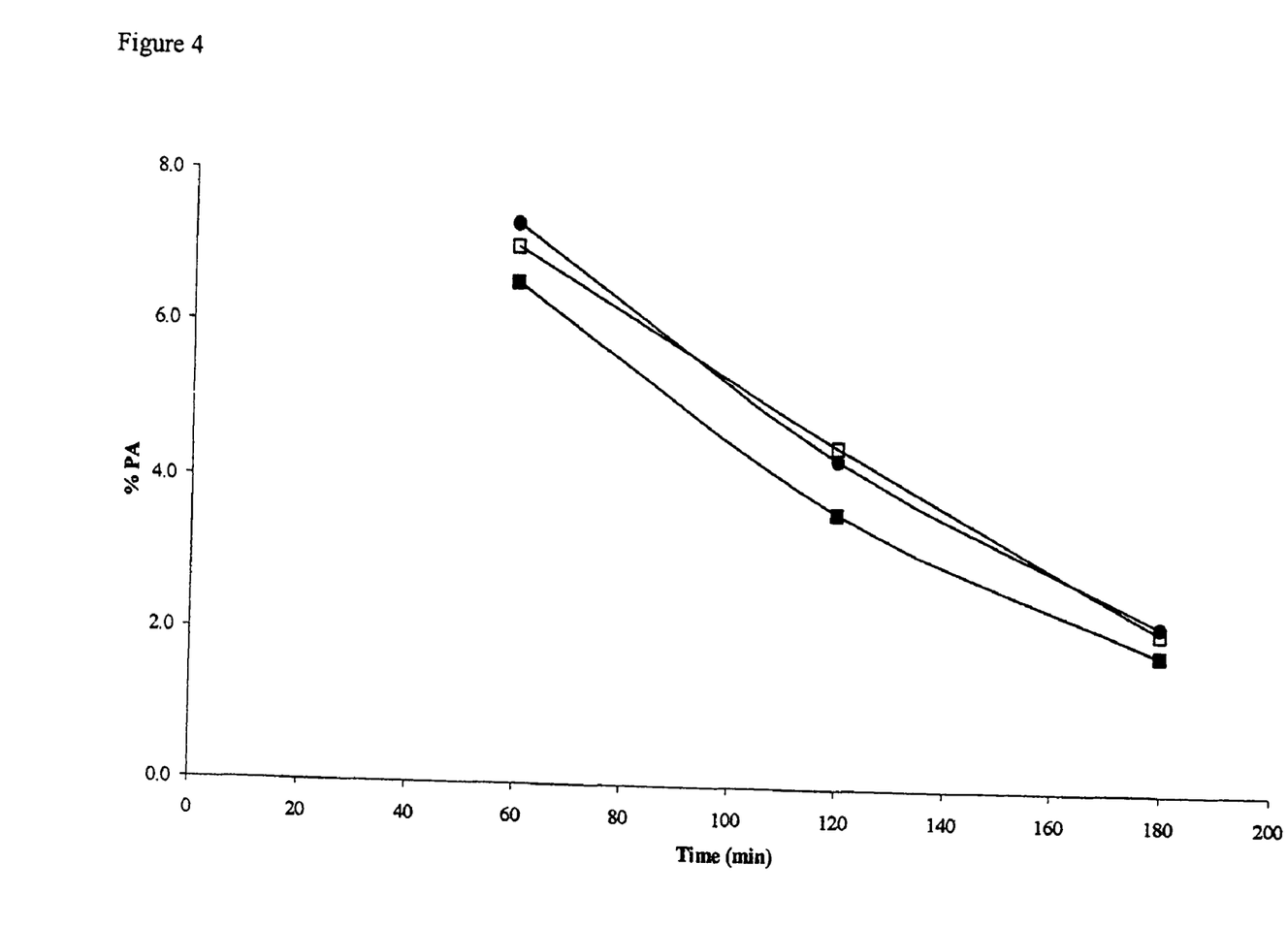
FIG. 4 is a graph depicting the esterification of palmitic acid in soybean oil with methanol (85° C.; PA:MeOH=1:20, catalyst is 10% SBA-15-SO$_3$H—P 123) showing the effect of external mass transfer (■=200 rpm, •=350 rpm, □=500 rpm).

Since the superiority of the $H_2SO_4$ catalyst in the reaction may be attributable to external mass transfer limitation with the solid catalysts, the esterification reaction was performed at a range of agitation speeds. Shown in FIG. 4 are the results for the SBA-15-$SO_3H$—P123 catalyst, which was the most active solid catalyst. While a slight decrease in conversion was noted at the lowest stirring rate, the results for the 350 and 500 rpm runs were the same demonstrating at the higher stirring rates that were used in the current study no significant external mass transfer limitations were experienced.

Determining the cause of the higher activity for the SBA-15-$SO_3H$—P123 catalyst comprises understanding of the relative importance of its higher active site concentration and its larger MPD, since both of these attributes could be contributing to the improved performance. To better evaluate these features, the reaction was performed at a range of temperatures from 65–120° C. These data were then used to calculate apparent activation energies for the catalysts. The apparent activation energies were calculated assuming a pseudo first-order reaction with respect to the palmitic acid given that methanol was present in excess and soybean oil was not significantly reacting. The linear regressions fit for the resulting values (0.95<R2<1) confirmed that the assumed first order kinetics were reasonable.

Figure 5:
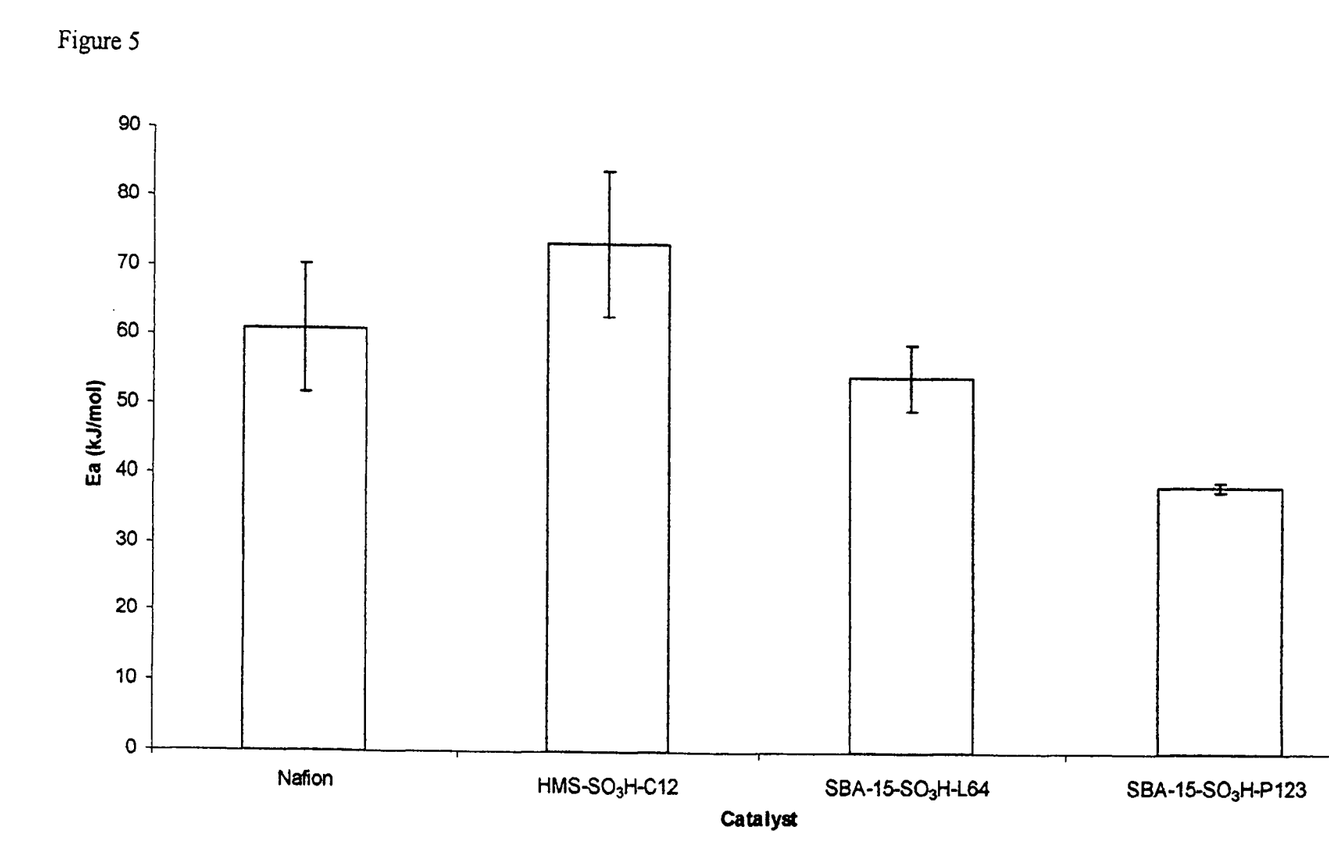
FIG. 5 is a graphical comparison of activation energy on the esterification of palmitic acid in soybean oil with methanol (PA:MeOH=1:20).

The calculated apparent activation energies are summarized in FIG. 5 for the three mesoporous silica catalysts as well as the Nafion. The apparent activation energy of the mesoporous catalysts decreased in the order of CDAB-$SO_3H$—C16>SBA-15-$SO_3H$-L64>SBA-15-$SO_3H$—P123. It is significant to note that the apparent activation energy was found to decrease with increasing MPD. If internal diffusion was not significantly limiting the catalyst, the apparent activation energies for these catalysts should be the same since the identical sulfonic acid functional group is the active site present in all the catalysts. The importance of the sulfonic acid groups in the conversion reaction was validated by running a mesoporous silica that contained a low level of grafted propylsulfonic acid groups (0.02 meq/g). This catalyst was nearly inactive for the esterification reaction indicating that the silica has no significant esterification activity.

A likely cause of the decreased apparent activation energy with increase in MPD is the importance of activated diffusion. The impact of activated diffusion on reaction kinetics has been amply demonstrated with zeolitic catalysts in which the activation energy of diffusion is strongly dependent on temperature and follows an Arrhenius relationship. In these systems activation energies of up to 84 kJ/mol have been reported for activated diffusion (S. Bhatia, "Zeolite Catalysts: Principles and Applications," CRL Press, FL (1990)). If the esterification reaction was limited by activated diffusion for the CDAB—SO$_3$H—C16 catalyst, subsequent increase in MPD as realized with the SBA-15 catalysts would lead to decreasing reaction limitation by activated diffusion. Therefore, the results in the current study appear to support the importance of activated diffusion in the esterification of palmitic acid with mesoporous materials having a MPD at least within the range of 22–35 Å.

Figure 2A:
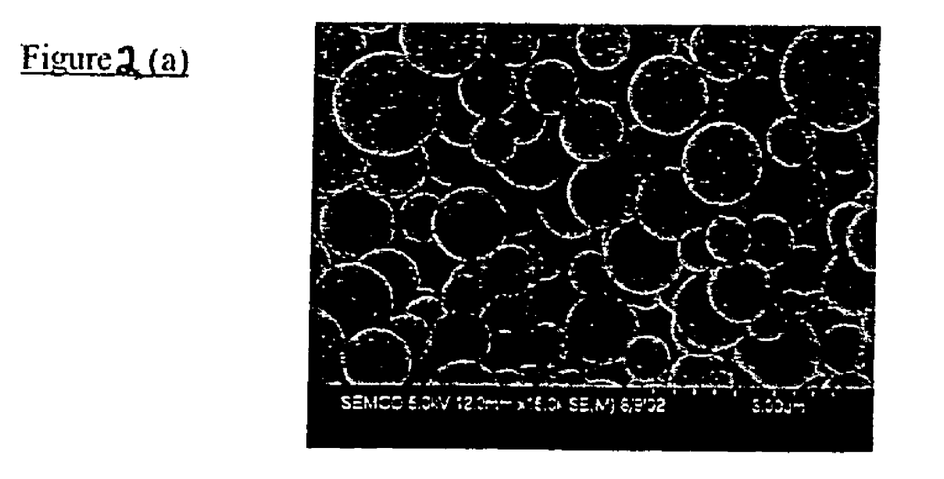
Figure 2B:
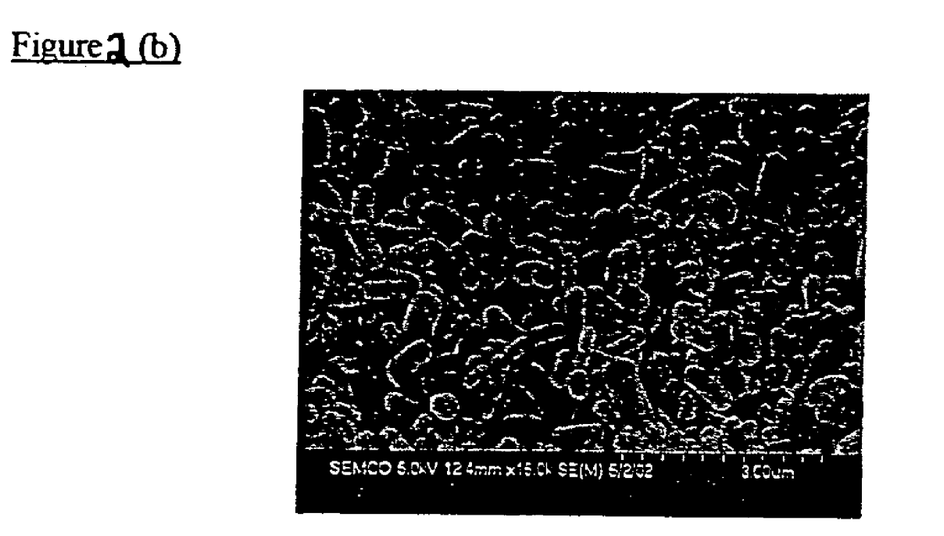

In addition to the accessibility of the acidic sites, a potentially important characteristic is the strength of the acid site. A more acidic catalyst was synthesized by introducing a phenyl group within the organosulfonic acid (FIG. 1b and FIG. 2b). The phenyl group, which is more electronegative than the aliphatic carbon chain, increases the acid strength of the sulfonic acid group within the catalyst. To diminish the possible effect of activated diffusion, arenesulfonic acid functionalized mesoporous silica was synthesized using Pluronic® P123, which is expected to yield a larger MPD than the other surfactants used in the study. The sample, which is denoted SBA-15-ph-SO$_3$H—P123, had the textural properties and the number of active sites as given in Table 1. Despite the use of a common surfactant template, this material had a larger MPD and pore volume than the SBA-15-SO$_3$H—P123 material. The difference in MPD may be attributable to the relative hydrophobicity of the arenesulfonic group relative to the propylsulfonic group. The higher hydrophobicity of the arenesulfonic group would favor a stronger intrusion of the group into the surfactant micelle causing a swelling of the micelle. This MPD result provides further evidence that the organosulfonic groups are covering the interior of the pores.

Figure 6:
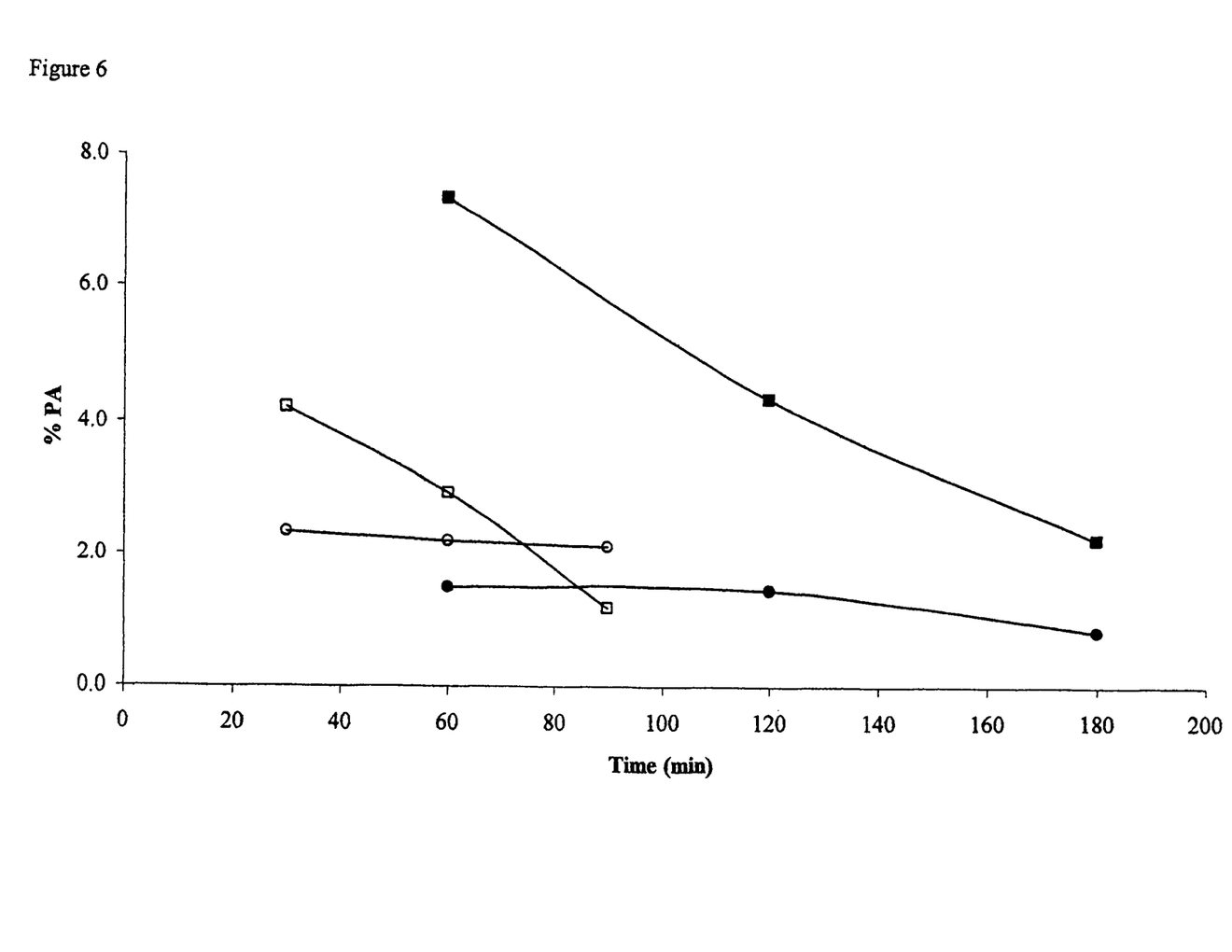
FIG. 6 is a graph depicting the esterification of palmitic acid with methanol (85° C.; PA:MeOH=1:20, catalyst: □=5% $H_2SO_4$, ○=10% pTSA, ■=10% SBA-5-$SO_3$H—P123, ●=10% SBA-5-ph-$SO_3$H—P123).

Shown in FIG. 6 is the catalytic activity of SBA-15-ph-SO$_3$H—P123 for the esterification of palmitic acid relative to SBA-15-SO$_3$H—P123 as well as the homogeneous catalysts H$_2$SO$_4$ and p-toluene sulfonic acid (pTSA). SBA-15-ph-SO$_3$H—P123 had significantly higher activity than SBA-15-SO$_3$H—P123 despite its lower number of acidic sites. In addition, it outperformed the esterification activity of the free pTSA. While the overall conversion achieved using SBA-15-SO$_3$H—P123 was similar to H$_2$SO$_4$, the initial reactivity of the solid catalyst was higher than for H$_2$SO$_4$. Esterification of free fatty acids (FFAs) with methanol releases water that is known to limit the extent of the esterification reaction. The low level of palmitic acid conversion after 60 minutes for SBA-15-SO$_3$H—P123 might be due to the presence of water with water potentially having a more detrimental impact on the performance of the solid catalyst than the homogeneous catalyst.

Figure 7:
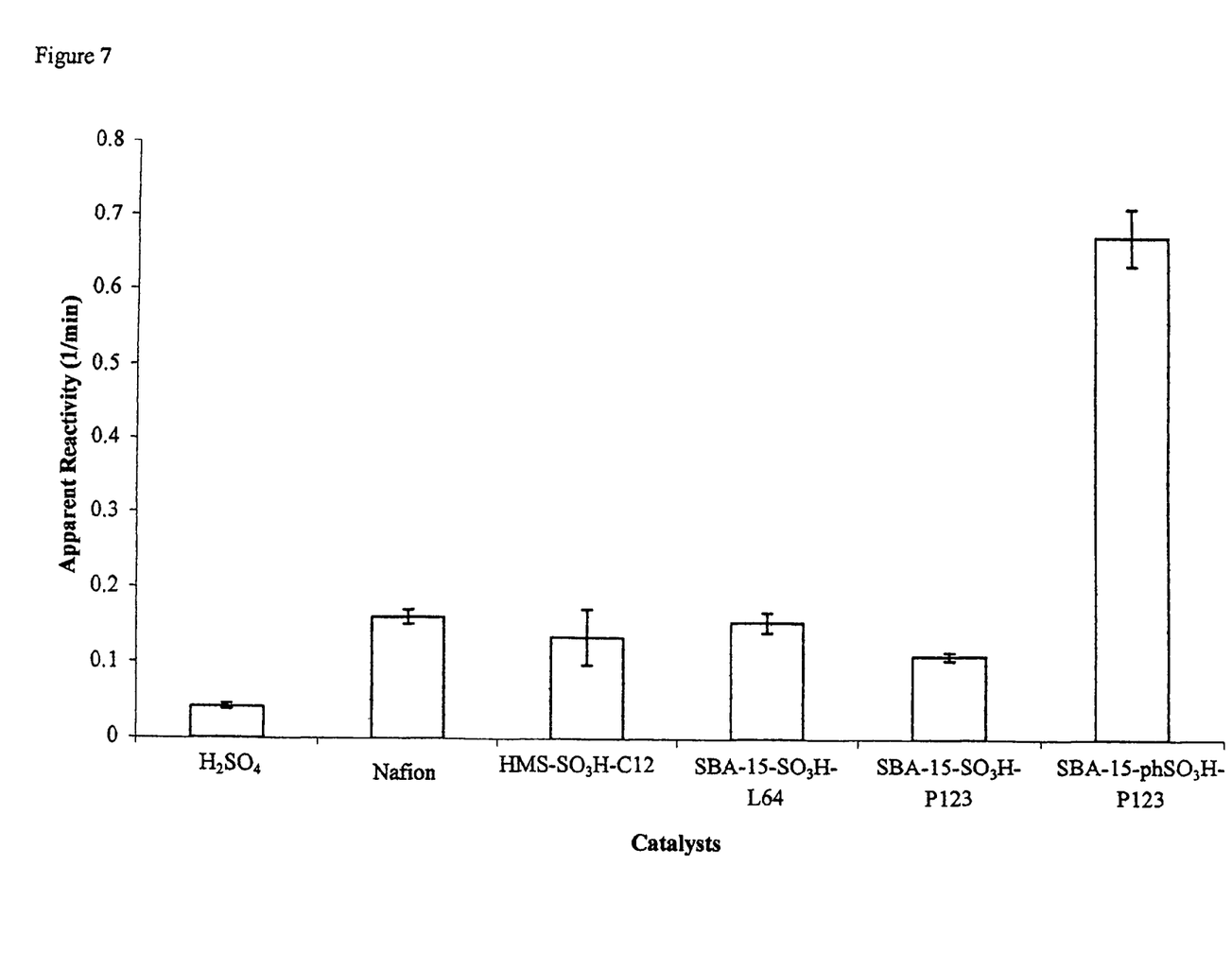
FIG. 7 is a graph comparing the apparent reactivity of the palmitic acid esterifying catalysts (85° C.; PA:MeOH=1:20).

Comparison of the reaction performance of catalysts relative to a mass-based loading of the catalysts has limitations when catalysts with different number of active sites are considered. An apparent reactivity can be defined as the average turnover rate per total number of active sites. Since internal diffusion has been demonstrated to be significant in the mesoporous catalysts, the apparent reactivity can only represent an average turnover number that is convoluted with diffusion effects. For the current catalysts the number of active sites is defined by the H$^+$ equivalents in the catalyst. Using this definition, the apparent reactivities for the catalysts at 85° C. are given in FIG. 7. As can be seen from the figure, SBA-15-SO$_3$H—P123 gave significantly higher apparent reactivity than any of the other catalysts, while the apparent reactivities for all of the propylsulfonic acid functionalized silicas as well as the Nafion were comparable. The high apparent reactivity for SBA-15-SO$_3$H—P123 supports the conclusion that increasing the acidity of the sulfonic acid group enhances the reactivity of the material in the esterification reaction.

EXAMPLE 6

Transesterification of Soybean Oil

In a typical experiment, soybean oil (1.0 mL) was mixed with 5.0 mL methanol (Fisher) and the reaction was stirred at 1,000 rpm under heating at 75° C. Powdered catalyst (100.0 mg) were added to the reaction mixture. The reaction was allowed to reflux for 12 hours. The progress of the reaction was monitored by collecting aliquots every 20 minutes. The excess methanol in the aliquots was flash evaporated and the crude product was dissolved in 1 mL of CDCl$_3$ and analyzed by $^1$H NMR spectroscopy to determine the yield of methyl soyate.

Figure 8:
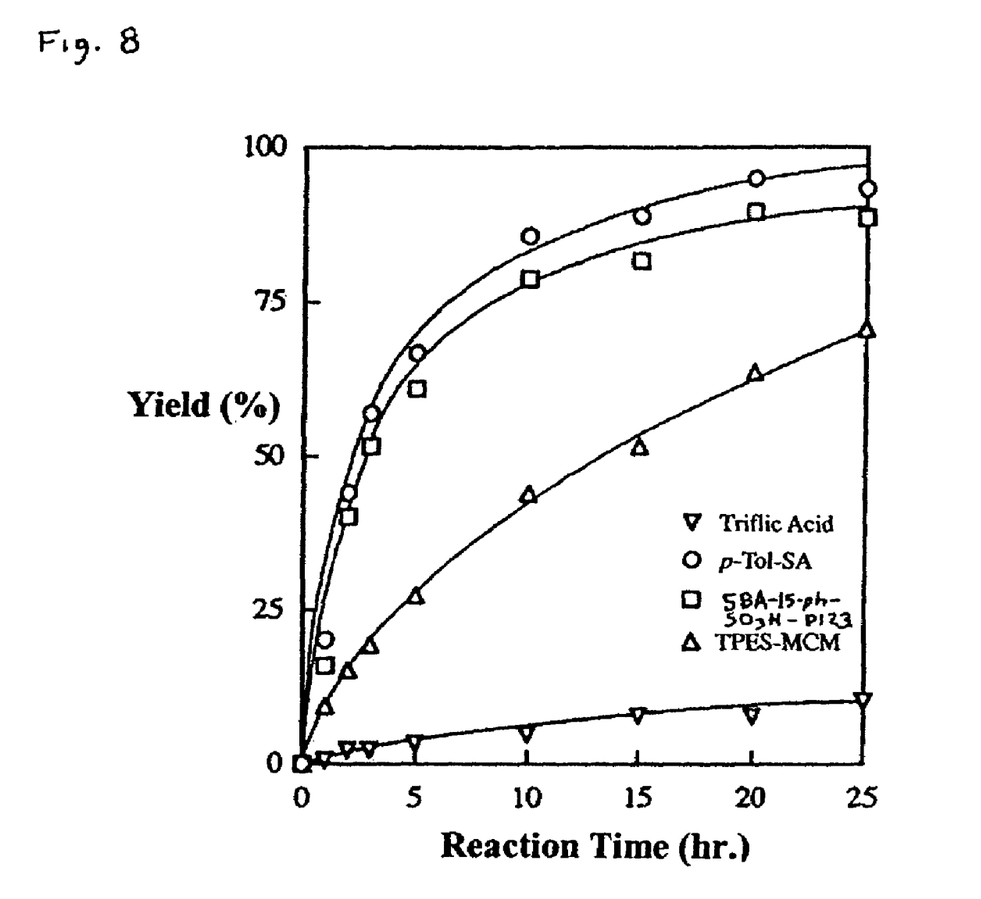
FIG. 8 is a graph depicting the reaction kinetics of the transesterification of soybean oil to methyl soyate (biodiesel) comprising fatty acid methyl esters and glycerol.

Recent catalytic studies of these alkane- and arene-sulfonic acid catalysts for transesterification of soybean oil to methyl soyate (biodiesel) showed that the presence of a phenyl group close to the sulfonic group significantly increases the acid strength in comparison to those with alkyl groups, and hence a significant enhancement of catalytic activity was observed as depicted in FIG. 8, wherein ∇=triflic acid; ○=p-toluenesulfonic acid (p-Tol-SA); □=MCM-41 silica functionalized with 4-(2-trimethoxysilyl)-ethylbenzenesulfonic acid groups (SBA-15-ph-SO$_3$H—P123) MCM); Δ=MCM-41 silica functionalized with 2-[3-(trimethoxysilyl)-propyldisulfanyl]-ethanesulfonic acid (TPES) (reaction temperature 75° C.).

In contrast to the high catalytic activity of the SBA-15-ph-SO$_3$H—P123 material, arenesulfonic acid-functionalized MCM-41 silica catalyst prepared by the postsynthesis grafting method gives rise to imhomogeneous surface coverage of the catalytic sulfonic acid groups and hence lower catalytic activity (three fold decrease relative to that of the P123 material). Such an inhomogeneous surface coverage of catalytic groups apparently inhibit or slow down the diffusion of both the reactants and products from accessing/leaving the catalytic sites. The results indicated that the ability of control and fine tune the location and surface density of the sulfonic acid catalytic groups is a crucial prerequisite for efficient conversion of the desired products. Also, the feasibility of tuning the acid strength of the sulfonic groups by close attachment of different functionalities might increase their potential catalytic applications. Therefore, the present synthetic methods can also be used to introduce various acid groups, such as maleic acid and perfluorosulfonic acid [Si(OCH$_3$)$_3$(CF$_2$)$_2$SO$_3$H], to the mesoporous silica surface to generate solid catalysts with different acid strengths for selective transesterification of soybean oil.

All publications, patents and patent applications are incorporated herein by reference. While in the foregoing specification this invention has been described in relation to certain preferred embodiments thereof, and many details have been set forth for purposes of illustration it will be apparent to those skilled in the art that the invention is susceptible to additional embodiments and that certain of the details described herein may be varied considerably without departing from the basic principles of the invention.

What is claimed:

1. A method for transesterifying an ester, comprising combining the ester, a $C_1$–$C_3$ alcohol, and an acidic mesoporous silicate under conditions wherein the mesoporous silicate catalyzes the formation of the ($C_1$–$C_3$) ester of the acid portion of the ester and the corresponding free alcohol of the ester, and wherein the silicate comprises sulfonic acids, sulfinic acids, phosphoric acids, phosphinic acids, boronic acids, selenic acids and mixtures thereof, linked to the silicate matrix by inert organic groups.

2. A method for preparing fatty acid ($C_1$–$C_3$) alkyl esters from a feedstock comprising one or more fatty acid glycerol esters and one or more fatty acids comprising combining the feedstock, a ($C_1$–$C_3$) alcohol, and an acidic mesoporous silicate under conditions wherein the mesoporous silicate catalyzes the formation of the corresponding fatty acid ($C_1$–$C_3$) alkyl esters, and wherein the silicate comprises sulfonic acids, sulfinic acids, phosphoric acids, phosphiic acids, boronic acids, selenic acids and mixtures thereof, linked to the silicate matrix by inert organic groups.

3. A method for producing a fatty acid ($C_1$–$C_3$) alkyl ester, comprising: combining a glyceride-containing vegetable or animal oil, a $C_1$–$C_3$ alcohol, and an acidic mesoporous silicate under conditions wherein the mesoporous silicate catalyzes formation of the corresponding fatty acid ($C_1$–$C_3$) alkyl ester and optionally, glycerol, and wherein the silicate comprises sulfonic acids, sulfinic acids, phosphoric acids, phosphinic acids, boronic acids, selenic acids and mixtures thereof, linked to the silicate matrix by inert organic groups.

4. A method for producing methyl soyate, comprising: combining soybean oil, methanol, and an acidic mesoporous silicate under conditions wherein the mesoporous silicate catalyzes formation of the methyl soyate and glycerol, and wherein the silicate comprises sulfonic acids, sulfinic acids, phosphoric acids, phosphinic acids, boronic acids, selenic acids and mixtures thereof, linked to the silicate matrix by inert organic groups.

5. A method for preparing a fatty acid ($C_1$–$C_3$) alkyl ester from a fatty acid comprising combining a fatty acid, a ($C_1$–$C_3$) alcohol, and an acidic mesoporous silicate under conditions wherein the mesoporous silicate catalyzes formation of the corresponding ($C_1$–$C_3$) alkyl ester, and wherein the silicate comprises sulfonic acids, sulfinic acids, phosphoric acids, phosphinic acids, boronic acids, selenic acids and mixtures thereof, linked to the silicate matrix by inert organic groups.

6. The method of claim 1, 2, 3, 4, or 5 wherein the acidic mesoporous silicate comprises immobilized sulfonic acid groups in the pores thereof, and optionally, comprises covalently bound ($C_1$–$C_3$) alkyl Si moieties as well.

7. The method of claim 6 wherein the inert organic groups comprise alkyl, fluoroalkyl, alkenyl, aratkyl, alkaryl, aryl, fluoroaryl, arylalkenyl, alkenylaryl or aralkenyl groups, wherein alkyl is optionally interrupted by —S—S, amido, —O— or ester.

8. The method of claim 1 wherein the ester comprises a $C_8$–$C_{22}$ fatty acid ester.

9. The method of claim 1 wherein the ester is a mono-, di- or tri-ester of glycerol.

10. The method of claim 9 wherein the ester is a tri-ester of glycerol.

11. The method of claim 10, wherein the tri-ester comprises one or more $C_8$–$C_{22}$ fatty acid esters.

12. The method of claim 1 wherein the ester is a glyceride in a vegetable oil.

13. The method of claim 12 wherein the ester is a glyceride in soybean oil.

14. The method of claim 1, 2, 3 or 5 wherein the $C_1$–$C_3$ alcohol is methanol or ethanol.

15. The method of claim 14 wherein the $C_1$–$C_3$ alcohol is methanol.

16. The method of claim 1, 2, 3, 4 or 5 wherein the formation of the ester is carried out at a temperature of less than about 150° C.

17. The method of claim 7 wherein alkyl is ($C_2$–$C_{10}$)alkyl.

18. The method of claim 7 or 17, wherein aryl is ($C_8$–$C_{10}$) aryl.

19. The method of claim 1, 2, 3, 4 or 5 wherein the formation of the ester is carried out without added solvent.

* * * * *

UNITED STATES PATENT AND TRADEMARK OFFICE
CERTIFICATE OF CORRECTION

PATENT NO. : 7,122,688 B2 Page 1 of 1
APPLICATION NO. : 10/945559
DATED : October 17, 2006
INVENTOR(S) : Lin et al.

It is certified that error appears in the above-identified patent and that said Letters Patent is hereby corrected as shown below:

In column 4, line 65, delete "P 123" and insert -- P123 --, therefor.

In column 5, line 56, delete "–0–"and insert -- –O– --, therefor.

In column 8, line 58, after "ArH)" insert -- , --.

In column 9, line 5, after "$CH_2(3)$" insert -- ) --.

In column 9, line 55, delete "Sigmna" and insert -- Sigma --, therefor.

In column 12, line 13, after "182" insert -- , --.

In column 15, line 20, in Claim 2, delete "phosphiic" and insert -- phosphinic --, therefor.

In column 16, line 12, in Claim 7, delete "aratkyl" and insert -- aralkyl --, therefor.

Signed and Sealed this

Twenty-fourth Day of April, 2007

JON W. DUDAS
*Director of the United States Patent and Trademark Office*